(12) United States Patent
Fukumura et al.

(10) Patent No.: US 6,344,579 B1
(45) Date of Patent: Feb. 5, 2002

(54) PROCESS FOR PRODUCING FLUORINATED SILICON COMPOUND

(75) Inventors: Kouki Fukumura, Fukuoka; Takashi Shimaoka, Chiba; Hideaki Oikawa, Fukuoka; Hiroshi Sonoda, Fukuoka; Ken'ichi Goto, Fukuoka; Junko Naruse, Fukuoka; Hidetoshi Hayashi, Fukuoka; Tsuyoshi Yasutake, Chiba, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/831,146

(22) PCT Filed: Sep. 12, 2000

(86) PCT No.: PCT/JP00/06224

§ 371 Date: May 7, 2001

§ 102(e) Date: May 7, 2001

(87) PCT Pub. No.: WO01/21528

PCT Pub. Date: Mar. 29, 2001

(30) Foreign Application Priority Data

Sep. 17, 1999 (JP) ............................. 11-262847
Oct. 26, 1999 (JP) ............................. 11-303220

(51) Int. Cl.$^7$ .................................................. C07F 7/08
(52) U.S. Cl. ...................................................... 556/477
(58) Field of Search ........................................ 556/477

(56) References Cited

U.S. PATENT DOCUMENTS

| | | | | |
|---|---|---|---|---|
| 3,408,380 A | * | 10/1968 | Pittman et al. | 556/477 |
| 3,507,799 A | * | 4/1970 | Hart | 556/477 |
| 3,525,763 A | * | 8/1970 | Muller et al. | 556/477 |
| 3,621,045 A | * | 11/1971 | Muller et al. | 556/477 |
| 3,646,092 A | * | 2/1972 | Dathe et al. | 556/477 |
| 3,655,714 A | * | 4/1972 | Dathe et al. | 556/477 |
| 5,466,850 A | * | 11/1995 | Alty et al. | 556/477 |
| 5,468,894 A | * | 11/1995 | Yamaguchi et al. | 556/477 |

FOREIGN PATENT DOCUMENTS

EP 0895991 2/1999

OTHER PUBLICATIONS

Omar Farooq, "Nucleophilic fluorinations of alkoxysilane with alkali metal hexafluorophosphate–part 1", Journal of Fluorine Chemistry, 1997, pp. 189–197.

* cited by examiner

*Primary Examiner*—Paul F. Shaver
(74) *Attorney, Agent, or Firm*—Burns, Doane, Swecker & Mathis, L.L.P.

(57) ABSTRACT

There is disclosed a convenient and efficient process for producing a fluorinated silicon compound which comprises reacting a silicon compound having at least one group selected from the group consisting of a hydroxyl group, an alkoxy group, and an aryloxy group bonded to silicon atom, with a compound represented by the formula (1):

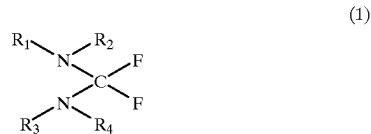

(1)

wherein $R_1$, $R_2$, $R_3$, and $R_4$ may be the same or different, and each represents a substituted or unsubstituted, saturated or unsaturated alkyl group, or a substituted or unsubstituted aryl group; and $R_1$ and $R_2$ or $R_3$ and $R_4$ can bond to form a ring having one or more nitrogen atoms or having one or more nitrogen atoms and other hetero atoms; or $R_1$ and $R_3$ can bond to form a ring having two or more nitrogen atoms or having two or more nitrogen atoms and other hetero atoms, to fluorinate the groups.

5 Claims, No Drawings

PROCESS FOR PRODUCING FLUORINATED SILICON COMPOUND

TECHNICAL FIELD

The present invention relates to a process for producing a fluorine-containing compound by fluorination of a hydroxyl group, an alkoxy group, or an aryloxy group. More particularly, it relates to a novel process for producing a fluorinated silicon compound by reacting a silicon compound in which at least one group selected from the group consisting of a hydroxyl group, an alkoxy group, and an aryloxy group is bonded to silicon atom, with a fluorinating agent, to fluorinate these groups.

BACKGROUND OF THE INVENTION

Many studies have hitherto carried out with regard to fluorination of a hydroxyl group (also called a silanol group), an alkoxy group, or an aryloxy group bonded to silicon atom, but the known processes have problems to be solved in view of safety of the reagents, convenience of the reaction, and the like.

For example, it is described in Anal. Chem. vol. 58, 499–501(1986) that dimethylaminosulfurtrifluoride (DAST) causes substitution of almost 50% of a silanol group (hydroxyl group bonded to silicon) on the surface of silica by fluorine.

DAST, a four-valent sulfur compound not only causes effective substitution of a hydroxyl group of primary, secondary, and tertiary alcohols by fluorine under mild conditions but also is a useful compound as a fluorinating agent for oxygen-containing functional groups such as a carboxyl group and a carbonyl group [U.S. Pat. No. 3,976,691].

However, DAST is produced by reacting highly dangerous sulfur tetrafluoride and diethylaminotrimethylsilane at a low temperature of −78 to −60° C., and specific equipment is required. Also, in view of safety, there is a report that an explosion occurred in the production and use of DAST [J. Fluorine Chem., 42, 137 (1989)].

Moreover, it is described in Z. Chem. vol. 11, 382–384 (1971) that carbonyl fluoride ($COF_2$) has an effective reactivity as a fluorinating reagent for a hydroxyl group or an alkoxy group bonded to silicon atom.

However, carbonyl fluoride is a gas at ordinary temperature, has toxicity and danger of an explosion owing to its high reactivity, and thus is a chemical product which is difficult to handle.

Fluorination of silanol groups on silica surface with HF has been also reported [Teor. Eksp. Khim., 15(4), 400–405 (1979); EP 221780]. HF is an inexpensive fluorine source, but is difficult to handle owing to its harmfulness, and has a possibility of destroying the Si—Si bonds or Si—O bonds of the bulk.

In addition, there is a report that silanol group has been fluorinated with $TeF_6$ [J. Chem. Soc., Chem. Commun. (20), 1113(1972)].

However, $TeF_6$ has a low boiling point and is liable to hydrolysis. Also, Te is a trace element and is fairly expensive even as a simple substance.

Furthermore, a process for producing a fluorosilane by reacting an alkoxysilane with $MPF_6$ (M represents Li, K, or Na) is described in Journal of Fluorine Chemistry, vol. 86, 189–197 (1996). It is described that the reaction can be carried out in a yield as high as 90% or more according to the process, but the process has problems that $MPF_6$, a corrosive reagent, has to be treated at a high temperature of 200° C. and $MPF_6$ to be used as a fluorinating agent is expensive.

As other examples of the reaction of an alkoxy group with a phosphorus compound, there are known an example of using $R_nPF_{5-n}$ (n=0, 1, 2, or 3) as a fluorinating agent [Journal of Fluorine Chemistry, 1, 252–254 (1971/1972)], and an example of using $CH_3POF_2$ as a fluorinating agent [J. Org. Chem., 53, 3364–3365 (1988)]. However, both technologies require the improvement of the product yields and the stability of the fluorinating agents and reaction products.

DISCLOSURE OF THE INVENTION

The object of the present invention is to provide a process for producing a fluorinated silicon compound conveniently and effectively.

As a result of the extensive studies for accomplishing the above object, the present inventors have been found that a compound represented by the formula (1):

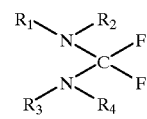

(1)

wherein $R_1$, $R_2$, $R_3$ and $R_4$ may be the same or different, and each represents a substituted or unsubstituted, saturated or unsaturated alkyl group, or a substituted or unsubstituted aryl group; and $R_1$ and $R_2$ or $R_3$ and $R_4$ can bond to form a ring having one or more nitrogen atoms or having one or more nitrogen atoms and other hetero atoms; or $R_1$ and $R_3$ can bond to form a ring having two or more nitrogen atoms or having two or more nitrogen atoms and other hetero atoms; serves an excellent effect as a novel fluorinating agent capable of replacing a hydroxyl group, an alkoxy group, or an aryloxy group bonded to silicon atom with fluorine atom, and the operations from the production of the fluorinating agent to its use in fluorination can be carried out extremely safely and easily without requiring any specific equipments. Based on the findings, they have accomplished the invention.

That is, the invention relates to the following.

(1) A process for producing a fluorinated silicon compound which comprises reacting a silicon compound having at least one group selected from the group consisting of a hydroxyl group, an alkoxy group, and an aryloxy group bonded to silicon atom, with a compound represented by the formula (1):

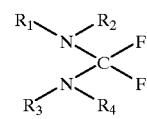

(1)

wherein $R_1$, $R_2$, $R_3$ and $R_4$ may be the same or different, and each represents a substituted or unsubstituted, saturated or unsaturated alkyl group, or a substituted or unsubstituted aryl group; and $R_1$ and $R_2$ or $R_3$ and $R_4$ can bond to form a ring having one or more nitrogen atoms or having one or more nitrogen atoms and other hetero atoms; or $R_1$ and $R_3$ can bond to form a ring having two or more nitrogen atoms or having two or more nitrogen atoms and other hetero atoms, to fluorinate the groups.

(2) The process for producing a fluorinated silicon compound as described in the above (1), wherein the compound represented by the formula (1) is a compound represented by the formula (2):

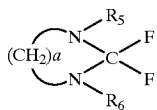

(2)

wherein a is an integer of 2 or 3, and $R_5$ and $R_6$ may be the same or different and each represents a substituted or unsubstituted, saturated or unsaturated lower alkyl group having 1 to 6 carbon atoms.

(3) The process for producing a fluorinated silicon compound as described in the above (2), wherein the compound represented by the formula (2) is 2,2-difluoro-1,3-dimethylimidazolidine represented by the formula (3):

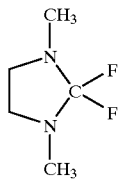

(3)

(4) The process for producing a fluorinated silicon compound as described in the above (1), wherein the silicon compound having at least one group selected from the group consisting of a hydroxyl group, an alkoxy group, and an aryloxy group bonded to silicon atom, is a compound represented by the formula (5):

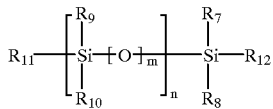

(5)

wherein $R_7$, $R_8$, $R_9$, $R_{10}$, $R_{11}$ and $R_{12}$ each represents an alkyl group having 1 to 6 carbon atoms, an aryl group, hydrogen atom, hydroxyl group, an alkoxy group having 1 to 6 carbon atoms, or an aryloxy group, provided that at least one of $R_7$, $R_8$, $R_9$, $R_{10}$, $R_{11}$, and $R_{12}$ is hydroxyl group, an alkoxy group having 1 to 6 carbon atoms, or an aryloxy group; n represents an integer of 0 to 100; and m represents 0 or 1.

(5) The process for producing a fluorinated silicon compound as described in the above (1), wherein the silicon compound having at least one group selected from the group consisting of a hydroxyl group, an alkoxy group and an aryloxy group bonded to silicon atom, is a silica having at least one of these groups.

In the invention, starting with the silicon compound having at least one group selected from the group consisting of a hydroxyl group, an alkoxy group and an aryloxy group (hereinafter, simply referred to as the hydroxyl group, alkoxy group and/or aryloxy group") bonded to silicon atom, a fluorinated silicon compound can be produced by replacing the hydroxyl group, alkoxy group and/or aryloxy group bonded to silicon atom of the silicon compound with fluorine atom using the compound represented by the formula (1).

This process realizes a high selectivity, safety and easiness to handle. Moreover, the fluorinating agent can be used without using highly dangerous chemicals and without requiring a specific equipments to produce fluorinated silicon compounds safely and easily as well as economically.

Accordingly, the process of the invention is useful as an industrial process for producing a fluorinated silicon compound, which solves the problems at the conventional processes.

BEST MODE FOR CARRYING OUT THE INVENTION

Hereinafter, the present invention will be illustrated in detail.

The fluorinating agent according to the invention is a compound represented by the formula (1):

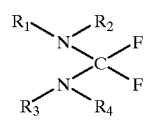

(1)

wherein $R_1$ to $R_4$ are the same as described above.

In the formula (1), $R_1$ to $R_4$ may be the same or different and each represents a substituted or unsubstituted, saturated or unsaturated alkyl group, or a substituted or unsubstituted aryl group; and $R_1$ and $R_2$ or $R_3$ and $R_4$ can bond to form a ring having one or more nitrogen atoms or having one or more nitrogen atoms and other hetero atoms. Preferred is an alkyl group having 1 to 6 carbon atoms or an aryl group, and the alkyl group may be linear or branched. Specifically, examples include methyl group, ethyl group, n-propyl group, isopropyl group, n-butyl group, butenyl group, n-hexyl group, phenyl group and the like, and the alkyl groups may be the same or different.

Moreover, $R_1$ and $R_2$ or $R_3$ and $R_4$ each can bond to form a heterocyclic ring having one or more nitrogen atoms, preferably having 3 to 5 carbon atoms. Examples of such a ring include pyrrolidine ring and piperidine ring.

Furthermore, $R_1$ and $R_3$ can bond to form a 5-membered or 6-membered heterocyclic ring having two nitrogen atoms. Examples of such a ring include imidazolidine ring, imidazolidinone ring, pyrimidine ring, and pyrimidinone ring.

As the compound represented by the formula (1), the compound in which $R_1$ and $R_3$ are combined to form a ring containing two nitrogen atoms is a compound represented by the formula (2):

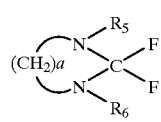

(2)

wherein a is an integer of 2 or 3, and $R_5$ and $R_6$ may be the same or different and each represents a substituted or unsubstituted, saturated or unsaturated lower alkyl group having 1 to 6 carbon atoms, preferably, 2,2-difluoro-1,3-dimethylimidazolidine represented by the formula (3):

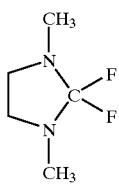

(3)

As the compound represented by the formula (1), specifically the following compounds may be mentioned but the invention is not limited to these examples.

Examples includes bis-dimethylamino-difluoromethane, bis-diethylamino-difluoromethane, bis-di-n-propylamino-difluoromethane, bis-diisopropylamino-difluoromethane, bis-di-allylamino-difluoromethane, bis-di-n-butylamino-difluoromethane, bis-n-hexylamino-difluoromethane, bis-(1-prrolidyl)-difluoromethane, bis-(1-piperidyl)-difluoromethane, 2,2-difluoro-1,3-dimethyl-imidazolidine, 2,2-difluoro-1,3-diethyl-imidazolidine, 2,2-difluoro-1,3-di-n-propyl-imidazolidine, 2,2-difluoro-1,3-diisopropyl-imidazolidine, 2,2-difuluoro-1,3-diallyl-imidazolidine, 2,2-difluoro-1,3-di-n-butyl-imidazolidine, bis-(N-methyl-N-phenyl)-difluoromethane, 2,2-difluoro-1,3-di-n-butyl-imidazolidin-4,5-dione, and 2,2-difluoro-1,3-dimethylpyrimidine.

Particularly preferred is 2,2-difluoro-1,3-dimethyl-imidazolidine represented by the above formula (3).

The compound represented by the formula (1) according to the invention can be produced by the following process. Namely, the compound can be obtained safely and easily by exchanging halogens of a compound represented by the formula (4):

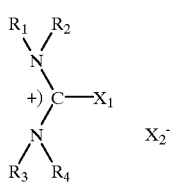

(4)

wherein $X_1$ and $X_2$ may be the same or different and each represents chlorine or bromine atom; $R_1$, $R_2$, $R_3$, and $R_4$ may be the same or different, and each represents a substituted or unsubstituted, saturated or unsaturated alkyl group, or a substituted or unsubstituted aryl group; and $R_1$ and $R_2$ or $R_3$ and $R_4$ can bond to form a ring having one or more nitrogen atoms or having one or more nitrogen atoms and other hetero atoms; or $R_1$ and $R_3$ can bond to form a ring having two or more nitrogen atoms or having two or more nitrogen atoms and other hetero atoms, with an alkali metal fluoride in an inert solvent.

As the alkali metal fluoride, cesium fluoride, rubidium fluoride, potassium fluoride, sodium fluoride, and the like can be used, and preferred is potassium fluoride for fluorination which is advantageous in view of economy and reaction-efficiency.

As the compound represented by the formula (4), a compound wherein $X_1$ and $X_2$ are chlorine atoms is usually used but a compound wherein either or both of them are bromine atoms can be also used with no problem.

Specific examples thereof include a tetraalkylchloroformamidium chloride, a 2-chloro-1,3-dialkylimidazolium chloride, a 2-bromo-1,3-dialkylimidazolium bromide, and the like.

The compound of the formula (4) to be used as a raw material for producing the compound represented by the formula (1) can be produced, for example, by halogenating a tetraalkylurea, a tetraalkylthiourea, an N,N'-dialkylimidazolidinone, an N,N'-dialkylimidazolidin-2-thione, or the like with a halogenating agent such as phosgene, thionyl chloride, thionyl bromide, phosphorus trichloride, or phosphorus tribromide.

For example, 1,3-dimethyl-2-chloroimidazolium chloride can be easily produced by the method described in Japanese Patent Laid-Open No. 25375/1984. Alternatively, it can be also produced by adding dropwise a solution of oxalyl chloride dissolved in a solvent such as carbon tetrachloride to 1,3-dimethylimidazolidinone and reacting them at room temperature to 60° C. for several hours to several ten hours.

In the production of the compound represented by the formula (1) of the invention, the amount of the alkali metal fluoride to be used for the halogen exchange is preferably 2 equivalents or more, more preferably 2 to 5 equivalents to the tetraalkyl-haloformamidium halide. When the amount is less than 2 equivalents, the exchange proceeds only incompletely and unexchanged halaide remains. Even when the fluoride is used in an amount exceeding 5 equivalents, the reaction yield is not so largely improved.

The reaction solvent is not particularly limited as long as the solvent does not react with both the tetraalkyl-haloformamidinium halide and the compound to be produced.

Preferred are acetonitrile, dimethylformamide, 1,3-dimethyl-2-imidazolidinone, dichloromethane, ethylene dichloride, and the like.

The amount of the reaction solvent is not particularly limited but, in view of the reaction efficiency and operationality, preferably it is usually from 1 to 100 times by weight as much as the reaction substrate.

The reaction temperature is not particularly limited but, in view of the reaction rate and stability of the product, it is usually in the range of −20 to 150° C., preferably 0 to 100° C.

However, in the case that the fluorine compound to be produced has a low boiling point or possesses a structure which tends to occur dehydrofluorination, the reaction temperature should be made low as far as possible. The fluorine compound produced during the reaction can be isolated from the reaction mixture by a general unit operation, for example, distillation, extraction, or the like.

The halogen exchange in the process for producing the compound represented by the formula (1) according to the invention can be carried out in the presence of a phase transfer catalyst such as a quaternary alkylammonium salt or a quaternary alkylphosphonium salt.

The compound represented by the formula (1) thus obtained can be used at the successive fluorination in the form of the reaction solution of the halogen exchange as it is, or in the form after removal of inorganic salts by filtration and evaporation of the reaction solvent, or in the form isolated by an operation such as distillation.

In the invention, the silicon compound having at least one group selected from the group consisting of a hydroxyl group, an alkoxy group, and an aryloxy group bonded to silicon atom means a compound wherein at least one group selected from the group consisting of a hydroxyl group, an alkoxy group, and an aryloxy group is directly bonded to the silicon atom in the silicon compound. These groups may be two or more groups which are the same or different.

More specifically, for example, the compound represented by the formula (5):

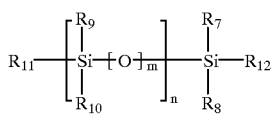

(5)

wherein $R_7$, $R_8$, $R_9$, $R_{10}$, $R_{11}$, and $R_{12}$ each represents an alkyl group having 1 to 6 carbon atoms, an aryl group, hydrogen atom, hydroxyl group, an alkoxy group having 1 to 6 carbon atoms, or an aryloxy group, provided that at least one of $R_7$, $R_8$, $R_9$, $R_{10}$, $R_{11}$, and $R_{12}$ is a hydroxyl group, an alkoxy group having 1 to 6 carbon atoms, or an aryloxy group; n represents an integer of 0 to 100; and m represents 0 or 1.

Specific examples of the compound represented by the formula (5) include trimethylsilanol, hydroxypentamethyldisiloxane, hydroxyheptamethyltrisiloxane, 1-hydroxynonamethyltetrasiloxane, hydroxypolydimethylsiloxane, triethylsilanol, hydroxypentaethyldisiloxane, hydroxyheptaethyltrisiloxane, hydroxynonaethyltetrasiloxane, hydroxypolydiethylsiloxane, triphenylsilanol, hydroxypentaphenyldisiloxane, hydroxyheptaphenyltrisiloxane, hydroxynonaphenyltetrasiloxane, hydroxypolydiphenylsiloxane, ethyldimethylsilanol, propyldimethylsilanol, t-butyldimethylsilanol, phenyldimethylsilanol, propyldiethylsilanol, t-butyldiethylsilanol, phenyldiethylsilanol, methyldiphenylsilanol, ethyldiphenylsilanol, propyldiphenylsilanol, t-butyldiphenylsilanol, dimethylsilanediol, 1,3-dihydroxytetramethyldisiloxane, 1,5-dihydroxyhexamethyltrisiloxane, 1,7-dihydroxyoctamethyltetrasiloxane, αω-dihydroxypolydimethylsiloxane, diethylsilanediol, 1,3-dihydroxytetraethyldisiloxane, 1,5-dihydroxyhexaethyltrisiloxane, 1,7-dihydroxyoctaethyltetrasiloxane, α,ω-dihydroxypolydiethylsiloxane, diphenylsilanediol, 1,3-dihydroxytetraphenyldisiloxane, 1,5-dihydroxyhexaphenyltrisiloxane, 1,7-dihydroxyoctaphenyltetrasiloxane, α,ω-dihydroxypolydiphenylsiloxane, trimethoxysilanol, triethoxysilanol, triphenoxysilanol, ethoxydimethylsilanol, propoxydimethylsilanol, t-butoxydimethylsilanol, phenoxydimethylsilanol, propyldiethoxysilanol, t-butyldiethoxysilanol, phenyldiethoxysilanol, methyldiphenoxysilanol, ethyldiphenoxysilanol, propyldiphenoxysilanol, t-butyldiphenoxysilanol, monomethoxysilane, monoethoxysilane, monopropoxysilane, monobutoxysilane, monophenoxysilane, trimethylmethoxysilane, triethylethoxysilane, tripropylpropoxysilane, tributylbutoxysilane, triphenylmethoxysilane, triphenylethoxysilane, triphenylpropoxysilane, triphenylbutoxysilane, triphenylphenoxysilane, diethoxysilane, dipropoxysilane, dibutoxysilane, diphenoxysilane, dimethyldimethoxysilane, diethyldiethoxysilane, dipropyldipropoxysilane, dibutyldibutoxysilane, diphenyldimethoxysilane, diphenyldiethoxysilane, diphenyldipropoxysilane, diphenyldibutoxysilane, diphenyldiphenoxysilane, trimethoxysilane, triethoxysilane, triprolpoxysilane, tributoxysilane, triphenoxysilane, methyltrimethoxysilane, ethyltriethoxysilane, propyltripropoxysilane, butyltributoxysilane, phenyltrimethoxysilane, phenyltriethoxysilane, phenyltripropoxysilane, phenyltributoxysilane, phenyltriphenoxysilane, dimethoxydisilane, diethoxydisilane, dipropoxydisilane, dibutoxydisilane, diphenoxydisilane, tetramethyldimethoxydisilane, tetraethyldiethoxydisilane, tetrapropyldipropoxydisilane, tetrabutyldibutoxydisilane, tetraphenyldimethoxydisilane, tetraphenyldiethoxydisilane, tetraphenyldipropoxydisilane, tetraphenyldibutoxydisilane, tetraphenyldiphenoxydisilane, dimethoxydisiloxane, diethoxydisiloxane, dipropoxydisiloxane, dibutoxydisiloxane, diphenoxydisiloxane, tetramethyldimethoxydisiloxane, tetraethyldiethoxydisiloxane, tetrapropyldipropoxydisiloxane, tetrabutyldibutoxydisiloxane, tetraphenyldimethoxydisiloxane, tetraphenyldiethoxydisiloxane, tetraphenyldipropoxydisiloxane, tetraphenyldibutoxydisiloxane, tetraphenyldiphenoxydisiloxane, and the like.

In addition, among the general silicon compounds, silica having at least one group selected from the group consisting of a hydroxyl group, an alkoxy group, and an aryloxy group bonded to silicon atom may be mentioned.

Silica is a compound constituted mainly by $SiO_2$ or its composition, and examples thereof include fine-particle silica, silica powder, silicalite, and the like. Such silica usually has hydroxyl group bonded to silicon atom. Also, as silica containing an alkoxy group and/or aryloxy group bonded to silicon atom, there may be mentioned silica synthesized starting with an alkoxysilane such as tetramethoxysilane and silica modified with a silane coupling agent such as trimethoxymethylsilane, for example. The shape of primary or secondary particles may be any of particle form, needle form, or amorphous form, and there is no limitation in the aggregation state. Furthermore, the shape of the aggregate is also not limited, and may be any of powder, granule, pellet, or a sintered one having any form, for example.

In the case of fluorination of a hydroxyl group, an alkoxy group, and/or an aryloxy group to silicon atom using the compound represented by the formula (1), the amount of the compound represented by the formula (1) to be used may be usually 1 equivalent or more to the hydroxyl group, the alkoxy group, and /or the aryloxy group bonded to silicon atom. The amount of less than 1 equivalent, it is not preferred because there is a possibility that unreacted hydroxyl group, alkoxy group, and/or aryloxy group may remain. Also, it is not preferred to use unnecessarily excessive amount from economical viewpoint. Therefore, the amount of the compound represented by the formula (1) is preferably from 1 to 5 equivalent, more preferably 1 to 3 equivalent to the hydroxyl group, alkoxy group, and/or aryloxy group bonded to silicon atom.

The silicon compound whose hydroxyl group, alkoxy group, and/or aryloxy group are fluorinated with the compound represented by the formula (1) is not restricted by functional groups, number of silicon atom, and number of hydroxyl group, alkoxy group, and/or aryloxy group bonded to single silicon atom. However, in the case that a substrate contains a functional group having an active hydrogen or hydroxyl group, alkoxy group, and/or aryloxy group other than the hydroxyl group, alkoxy group, and/or aryloxy group bonded to silicon atom, there is a possibility of occurrence of a side-reaction other than the replacement of the aimed hydroxyl group bonded to silicon atom with fluorine atom. For this reason, care must be taken because the necessary amount (equivalent) of the compound represented by the formula (1) required for the objective reaction varies.

Furthermore, the process for producing a fluorinated silicon compound can be also applied even to silicon compounds such as silicone resins, silicone greases, silicone rubbers, and silicon oils without any problem.

EXAMPLES

The following will explain the invention in more detail by reference to Examples but the invention is not limited thereto. In Synthetic Example, the concentration of 2,2-difluoro-1,3-dimethylimidazolidine (DFI) was measured by a high performance liquid chromatographic method after conversion of DFI into its derivative by the reaction with aniline.

The concentration of fluorine ion (hereinafter abbreviated as F—) was measured by an absorptiometric analysis using Alizarin Complexon reagent.

Synthetic Example

Synthesis of 2,2-difluoro-1,3-dimethyl-imidazolidine (DFI)

To a 500 ml, four-necked reaction flask 80.0 g (0.452 mol) of 1,3-dimethyl-2-chloro-imidazolium chloride, 105.1 g (1.810 mol) of spray-dried potassium fluoride, and 320 ml of acetonitrile were charged, and were reacted at 80° C. for 17 hours under a nitrogen atmosphere. The reaction mixture was cooled to 25° C. and then inorganic salts were separated from the reaction mixture to obtain 414.2 g of an acetonitrile solution of 2,2-difluoro-1,3-dimethylimidazolidine (MW 136.15). In the solution, the concentration of DFI was 11.4 wt % and the yield was 77%.

Concentration of F— in the solution Calculated value: 3.18 wt % Found value: 3.10 wt %

$^1$H-NMR ($\delta$, ppm, CH$_3$CN): 2.51 (s, 6H, —CH$_3$×2), 3.04 (s, 4H,—CH$_2$CH$_2$—); $^{13}$C-NMR ($\delta$, ppm, CH$_3$CN, −45° C.): 32.1 (s, —CH$_3$×2), 48.7 (s, —CH$_2$×2), 130.0 (t, J=230 Hz, —CF$_2$—); $^{13}$C-NMR ($\delta$, ppm, CH$_3$CN, 25° C.): 32.0 (s, —CH3×2), 48.7 (s, —CH$_2$—×2), 132.8 (broad, —CF$_2$— or =CF—)

Example 1

Synthesis of t-butyl-dimethyl-fluoro-silane

With 9 ml (about 12 g) of dichloromethane was mixed under stirring 1.2 g (about 9 mmol) of DFI isolated by distillation. To the solution was added dropwise 1.1 g (about 8.5 mmol) of t-butyl-dimethyl-silanol under ice-cooling. After completion of the addition, the whole was kept at room temperature for 1 hour under stirring. After completion of the reaction, formation of t-butyl-dimethyl-fluoro-silane was confirmed by GC-MS measurement of the reaction solution. The reaction yield was found to be 95% or more on GC analysis.

Example 2

Synthesis of diphenyl-difluoro-silane

With 14.6 ml (about 11.5 g) of acetonitrile was mixed under stirring 1.86 g (about 13.7 mmol) of DFI isolated by distillation. To the solution was added dropwise 1.4 g (about 5.1 mmol) of diethoxy-diphenyl-silane at room temperature. After completion of the addition, the whole was kept at room temperature for 1 hour under stirring. After the lapse of the reaction time, formation of diphenyl-difluoro-silane was confirmed by GC-MS measurement of the reaction solution. The reaction yield was found to be 95% or more on GC analysis.

Example 3

Reaction with fine-particle silica (fumed silica)

Into 100 ml of acetonitrile was dispersed 3 g of fine-particle silica having hydroxyl group bonded to silicon atom on the surface (surface silanol group) (fumed silica, compositional formula: SiO$_2$, AEROSIL, a product of Nippon Aerosil Co., Ltd. may be mentioned as a representative), a specific surface area of 200 m$^2$/g, and a surface silanol group concentration of 2 mmol/g. To the dispersion was added dropwise 3 g of DFI isolated by distillation, at room temperature under stirring. During the addition, the liquid temperature was temporarily raised to about 40° C. The mixture was left for 3.5 hours without cooling and heating. Thereafter, the fine-particle silica was filtered off and washed with acetonitrile. The fine-particle silica thus recovered was dried at 105° C. for 8 hours under reduced pressure (10 Torr).

The surface silanol group concentration of the fine-particle silica before and after the treatment was measured according to the method of Wartmann et al. described in Dissertation ETH Zurich (1958). As a result, the surface silanol group concentration was found to be 1.96 mmol/g before the treatment and 0.21 mmol/g after the treatment, and thus an decrease by the treatment was observed.

Furthermore, the fluorine content of the fine-particle silica after the treatment was measured by elementary analysis and found to be 3.4 wt %.

What is claimed is:

1. A process for producing a fluorinated silicon compound which comprises reacting a silicon compound having at least one group selected from the group consisting of a hydroxyl group, an alkoxy group, and an aryloxy group bonded to silicon atom, with a compound represented by the formula (1):

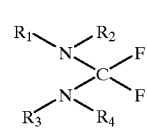

(1)

wherein R$_1$, R$_2$, R$_3$, and R$_4$ may be the same or different, and each represents a substituted or unsubstituted, saturated or unsaturated alkyl group, or a substituted or unsubstituted aryl group; and R$_1$ and R$_2$ or R$_3$ and R$_4$ can bond to form a ring having one or more nitrogen atoms or having one or more nitrogen atoms and other hetero atoms; or R$_1$ and R$_3$ can bond to form a ring having two or more nitrogen atom or having two or more nitrogen atoms and other hetero atoms, to fluorinate the groups.

2. The process for producing a fluorinated silicon compound according to claim 1, wherein the compound represented by the formula (1) is a compound represented by the formula (2):

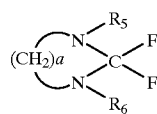

(2)

wherein a is an integer of 2 or 3, and $R_5$ and $R_6$ may be the same or different and each represents a substituted or unsubstituted, saturated or unsaturated lower alkyl group having 1 to 6 carbon atoms.

3. The process for producing a fluorinated silicon compound according to claim 2, wherein the compound represented by the general formula (2) is 2,2-difluoro-1,3-dimethylimidazolidine represented by the formula (3):

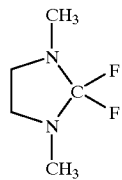

(3)

4. The process for producing a fluorinated silicon compound according to claim 1, wherein the silicon compound having at least one group selected from the group consisting of a hydroxyl group, an alkoxy group, and an aryloxy group bonded to silicon atom, is a compound represented by the formula (5):

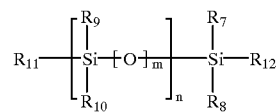

(5)

wherein $R_7$, $R_8$, $R_9$, $R_{10}$, $R_{11}$ and $R_{12}$ each represents an alkyl group having 1 to 6 carbon atoms, an aryl group, hydrogen atom, hydroxyl group, an alkoxy group having 1 to 6 carbon atoms, or an aryloxy group, provided that at least one of $R_7$, $R_8$, $R_9$, $R_{10}$, $R_{11}$, and $R_{12}$ is a hydroxyl group, an alkoxy group having 1 to 6 carbon atoms, or an aryloxy group; n represents an integer of 0 to 100; and m represents 0 or 1.

5. The process for producing a fluorinated silicon compound according to claim 1, wherein the silicon compound having at least one group selected from the group consisting of a hydroxyl group, an alkoxy group, and an aryloxy group bonded to silicon atom, is silica having at least one of these groups.

* * * * *